United States Patent [19]

Akimoto et al.

[11] Patent Number: 5,336,496
[45] Date of Patent: Aug. 9, 1994

[54] INHIBITOR FOR DELTA5-DESATURASE

[75] Inventors: Kengo Akimoto, Osaka; Yoshifumi Shinmen, Kyoto; Hideaki Yamada, Kyoto; Sakayu Shimizu, Kyoto; Michihiro Sugano, Fukuoka, all of Japan

[73] Assignee: Suntory Limited, Osaka, Japan

[21] Appl. No.: 867,086

[22] Filed: Apr. 14, 1992

Related U.S. Application Data

[63] Continuation of Ser. No. 488,997, Mar. 6, 1990, abandoned.

[30] Foreign Application Priority Data

Mar. 7, 1989 [JP] Japan ................................. 1-52950
Feb. 1, 1990 [JP] Japan ................................. 2-20469

[51] Int. Cl.$^5$ .................... A61K 35/78; A61K 31/675
[52] U.S. Cl. .................................. 424/195.1; 514/80; 514/885
[58] Field of Search ............... 424/195.1; 514/80, 783, 514/885

[56] References Cited

U.S. PATENT DOCUMENTS

| 113,713 | 4/1871 | Whitlow | 424/195.1 |
|---|---|---|---|
| 1,518,365 | 12/1924 | Shahapzian | 424/195.1 |
| 4,044,118 | 8/1977 | McCoy | 424/200 |
| 4,083,970 | 4/1978 | Large | 424/200 |
| 4,427,694 | 1/1984 | Benecke | 424/282 |
| 4,916,066 | 4/1990 | Akimoto | 435/134 |
| 4,970,076 | 11/1990 | Horrobin | 424/456 |

FOREIGN PATENT DOCUMENTS

| 0255287 | 7/1987 | European Pat. Off. . |
|---|---|---|
| 0322227 | 12/1988 | European Pat. Off. . |
| 0399494 | 5/1990 | European Pat. Off. . |

OTHER PUBLICATIONS

Mukhopadhyay, A., Antiinflammatory & Irritant Activities of Curcumin ..., Agents Actions 12(4) 1982 pp. 508–515.

Steinmetz G. F. Codex Vegetabilis 1957 Amsterdam Netherlands #370, 1056.

The Merck Index 10th Ed 1983 Merck & Co. Rahway N.J. pp. 1217, 1078, 382, 787.

Biological Abstract No. 85140218, Luini et al, "Inhibitors of the Cytochrome P-450 Enzymes Block the Secretagogue-Induced Release of Corticotropin in Mouse Pituitary ... ".

Biological Abstract No. 76059455, Mukhopadhyay et al, "Anti Inflammatory and Irritant Activities of Curcumin Analogs in Rats".

*Primary Examiner*—Michael G. Wityshyn
*Assistant Examiner*—Ralph Gitomer
*Attorney, Agent, or Firm*—Burns, Doane, Swecker & Mathis

[57] ABSTRACT

A composition for inhibiting $\Delta^5$-desaturase comprising an effective ingredient selected from the group consisting of lignan compounds, curcumin and piperonyl butoxide. As the lignan compounds sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, and 2-(3,4-methylenedioxyphenyl)-6-(3-methoxy-4-hydroxyphenoxy)-3,7-dioxabicyclo[3.3.0]-octane are used. Moreover the effective ingredient may be a sesame oil extract or sesame seed extract.

4 Claims, 3 Drawing Sheets

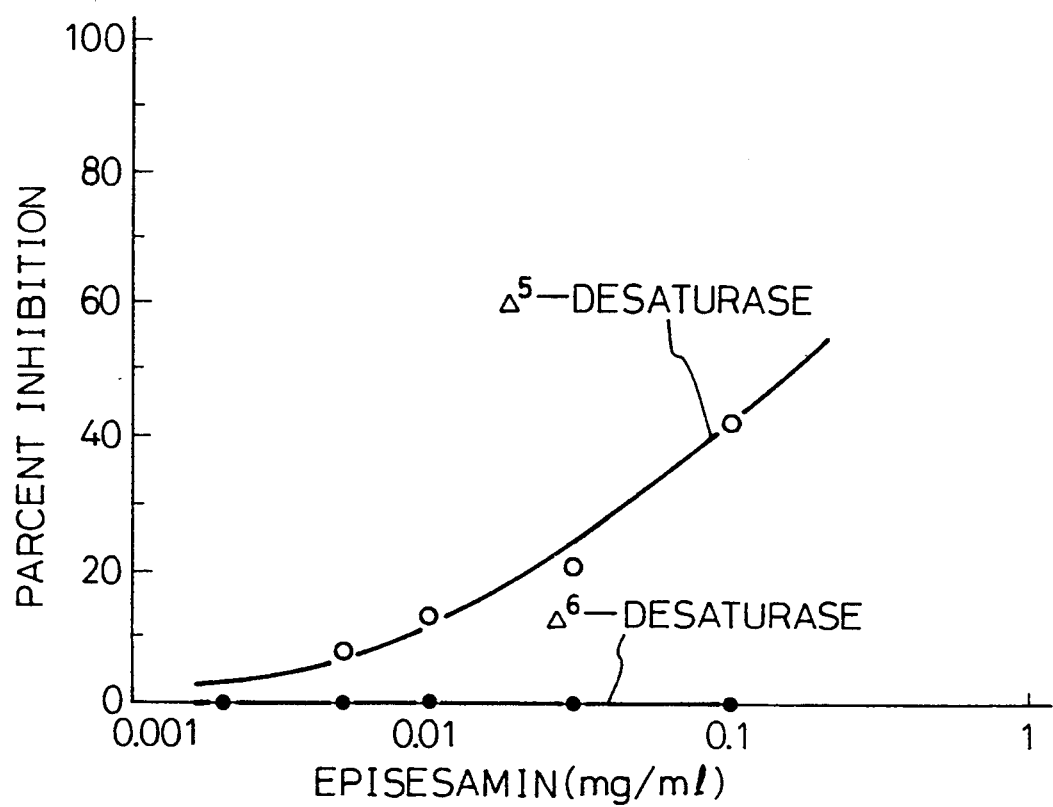

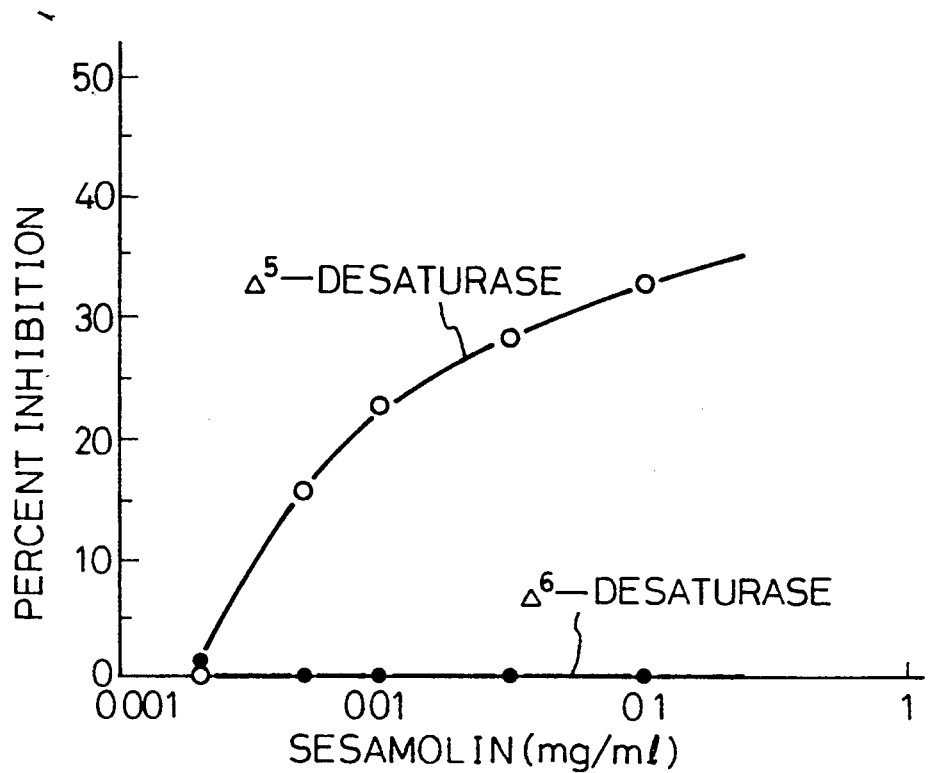

INHIBITOR FOR DELTA5-DESATURASE

This application is a continuation of application Ser. No. 07/488,997, filed Mar. 6, 1990 now abandoned.

BACKGROUND OF THE INVENTION

1. Field of the Invention

The present invention provides an inhibitor for $\Delta 5$-desaturase which specifically inhibits the conversion of dihomo-$\gamma$-linolenic acid to arachidonic acid. This inhibitor remarkably increases, in vivo, the amount of dihomo-$\gamma$-linolenic acid in comparison with arachidonic acid.

2. Description of the Related Art

Various studies relating to the actions of essential fatty acids on an organism show that not only are there two metabolic pathways for essential fatty acids, which pathways strongly influence each other, but also in the same metabolic pathway there are various metabolites which act antagonistically, and therefore, to enhance an action it is necessary not only to administer a related metabolite but also to inhibit an antagonistic action against the above-mentioned action. In the case of dihomo-$\gamma$-linolenic acid and a metabolite thereof, i.e., arachidonic acid, an eicosanoid derived from dihomo-$\gamma$-linolenic acid and an eicosanoid derived from arachidonic acid antagonistically influence each other, and therefore, to enhance the effects of an administration of dihomo-$\gamma$-linolenic acid, it is necessary to inhibit the conversion of dihomo-$\gamma$-linolenic acid to arachidonic acid. At present, although a series of prostaglandin 1 derived from dihomo-$\gamma$-linolenic acid is known to have an anti-thrombus activity, unless inhibiting the conversion of dihomo-$\gamma$-linolenic acid to arachidonic acid, the desired expected effect provided by administering dihomo-$\gamma$-linolenic acid is not obtained.

It is known that among lignan compounds, sesaminol, episesaminol, 2-(3,4-methylenedioxyphenyl) -6-(3-methoxy-4-hydroxyphenyl)-3,7-dioxabicyclo[3.3.0]-octane, 2,6-bis-(3-methoxy-4-hydroxyphenyl)-3,7 -dioxabicyclo[3.3.0]octane and 2-(3,4-methylene -dioxyphenyl)-6-(3-methoxy-4-hydroxyphenoxy)-3,7-dioxabicyclo[3.3.0]octane are comparable with or superior to sesaminol and $\gamma$-tocopherol in the antioxidation activity thereof, and are being developed as antioxidants. Moreover, these lignan compounds are under study for possible application for inhibition of lipid peroxidation in vivo which is considered a cause of senility, oncogenesis and the like. However, among lignan compounds, anti-oxidation activity of sesamin, episesamin and sesamolin is not known.

Moreover, it is not known that the above-mentioned lignan compounds inhibit $\Delta^5$-desaturase, which catalyzes the conversion of dihomo-$\gamma$-linolenic acid to arachidonic acid.

In addition, it is not known that curcumin and piperonyl butoxide inhibit $\Delta^5$- desaturase.

SUMMARY OF THE INVENTION

Accordingly, the present invention provides a composition for an inhibition of $\Delta^5$-desaturase, comprising a compound selected from the group consisting of lignan compounds, curcumin and piperonyl butoxide.

BRIEF EXPLANATION OF THE DRAWINGS

FIG. 2 is a graph showing that episesamin specifically inhibits $\Delta^5$-desaturase; and FIG. 3 is a graph showing that sesamolin specifically inhibits $\Delta^5$-desaturase.

DESCRIPTION OF THE PREFERRED EMBODIMENT

Figure 1:
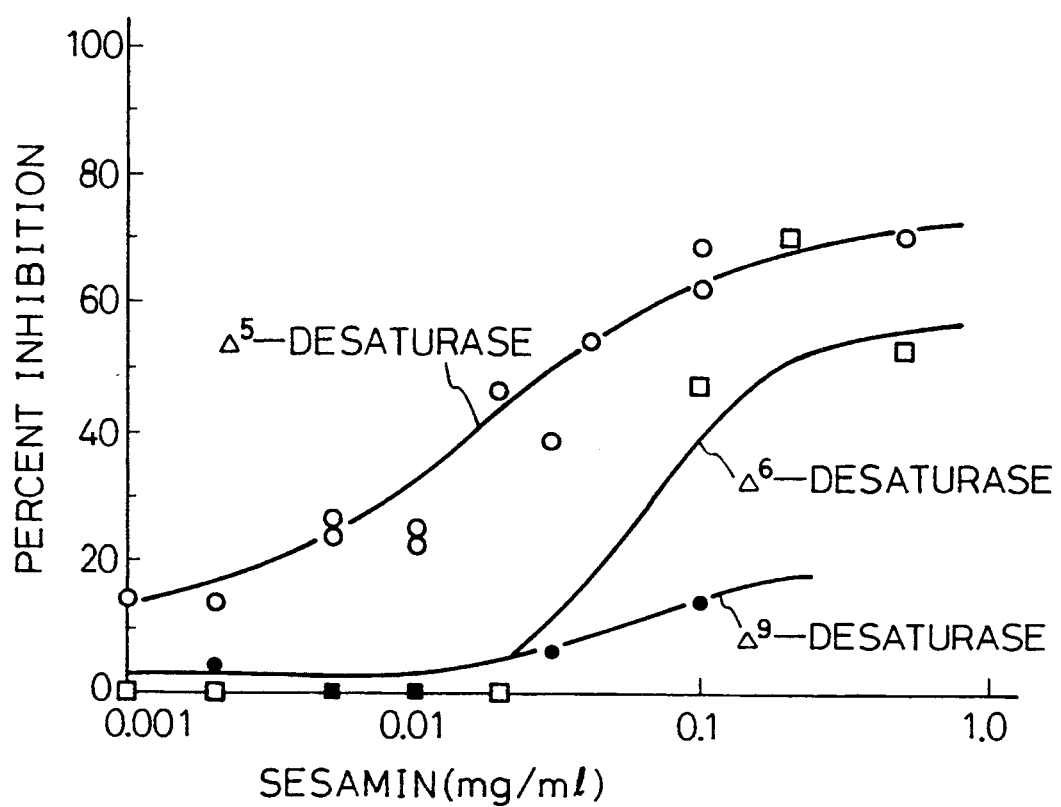
FIG. 1 is a graph showing that sesamin specifically inhibits $\Delta^5$-desaturase.

The present inventors found that lignan compounds, which inhibit $\Delta^5$-desaturase in a biosynthesis pathway for highly unsaturated fatty acids in arachidonic acid-producing microorganisms, also inhibit $\Delta^5$-desaturase in an enzyme cascade in rat liver microsome.

This inhibitory activity is provided by lignans such as sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis -(3-methoxy-4-hydroxyphenyl)-3,7-dioxabicyclo[3.3.0]octane and 2-(3,4-methylenedioxyphenyl)-6-(3-methoxy-4-hydroxyphenoxy)-3,7-dioxabicyclo[3.3.0]octane; curcumin of plant origin; as well as piperonyl butoxide which is a synergistic agent for agricultural chemicals.

The inhibition of the $\Delta^5$-desaturase increases the level of dihomo-$\gamma$-linolenic acid in vivo, which in turn increases levels of prostaglandin 1 series compounds through the enhancement of dihomo-$\gamma$-linolenic acid cascade. Namely, the increase of the dihomo-$\gamma$-linolenic acid level leads to an increase of the eicosanoid thereof, i.e., prostaglandin $G_1$ (PGG$_1$); prostaglandin $H_1$ (PGH$_1$); prostaglandin $D_1$ (PGD$_1$); prostaglandin $E_1$ (PGE$_1$); prostaglandin $F_{1\alpha}$(PGF$_{1\alpha}$); thromboxane $A_1$ (TXA$_1$); thromboxane $B_1$ (TXB$_1$); 12-(S)-hydroxy-8,10-pentadecadienic acid (HHD); 11-hydroperoxy-8,1 2,14-eicosatrienoic acid (11-HPETRE); 12-hydroperoxy-8,1 0,14-eicosatrienoic acid (12-HPETRE); 15-hydroperoxy-8,1 1,13-eicosatrienoic acid (15-HPETRE); 11-hydroxy-8,12,14 -eicosatrienoic acid (11-HETRE); 12-hydroxy-8,10,14 -eicosatrienoic acid (12-HETRE); 15-hydroxy-8,11,13 -eicosatrienoic acid (15-HETRE); 8-hydroperoxy-9,11 ,14-eicosatrienoic acid (8-HPETRE); 8-hydroxy-9,11,14-eicosatrienoic acid (8-HETRE); 8,9-leukotriene $A_3$ (8,9-LTA$_3$); 8,15-leukotriene $B_3$ (8,15-LTB$_3$); 8,9-leukotriene $C_3$ (8,9-LTC$_3$); 8,9-leukotriene $D_3$ (8,9-LTD$_3$); 8,9-leukotiene $E_3$ (8,9-LTE$_3$); 8,9-leukotriene $F_3$ (8,9-LTF$_3$), and the like.

These derived compounds provide advantageous activities. For example, it is known that PGE, exhibits anti-platelet aggregation activity, vasodilation activity, bronchodilation activity, and anti-inflammation activity, and are being studied for clinical application in the treatment of pulmonary trunk thrombosis, thromboembolism, pulmonary hypertension, bronchial asthma, congestive heart, new born blue disease, and skin diseases. Moreover, these compounds overcome the disadvantages that PGE$_1$, which having very strong biological activities, can be only partially absorbed as an active form in an oral administration of native prostaglandin (PG). This drawback is caused by an inactivation of PG at the wall of gastro-intestinal tract, and therefore, it has been considered that the development of a stable PG derivative or an injection of PG is necessary. Nevertheless, use of an inhibitor of $\Delta^5$-desaturase may regulate fatty acid biosynthesis in vivo, and provide various pharmacological activities, such as anti-inflammation activity, anti-thrombus activity, blood pressure-lowering activity and the like through increasing levels of dihomo-$\gamma$-linolenic acid and eicosanoids thereof.

Moreover, the above-mentioned active compounds are promising as functional factors for functional foods. Since the lignan compounds having an activity of inhibiting $\Delta^5$-desaturase are those inherently contained in edible oils, they are safe as functional factors for functional foods.

Lignan compounds as enzyme inhibitors of the present invention can be prepared, for example, as follows. First, an extract containing the lignans is obtained from sesame oil. The sesame oil may be purified sesame oil or crude sesame oil prior to a decoloring step. To obtain the extract, sesame oil is extracted with an organic solvent which is substantially immiscible with the sesame oil and can extract and dissolve effective ingredients. The organic solvents are, for example, acetone, methyl ethyl ketone, diethyl ketone, methanol, ethanol, and the like. To extract the effective ingredients, for example, sesame oil and the solvent are homogeneously mixed, and the mixture is allowed to stand at a low temperature, for example, $-80°$ C. Phases are separated by a conventional procedure such as centrifugation to obtain an organic phase, which is then evaporated to obtain an extract. Next, individual compounds can be isolated from the extract. To this end, the extract can be separated by a conventional procedure, such as column chromatography, high performance liquid chromatography, distillation, crystallization, or a combination thereof. More specifically, the extract is subjected to high performance liquid chromatography using a reverse column ($5C_{18}$) and an eluate, i.e., methanol/water (60:40) to obtain fractions containing the desired lignans. After distilling off the solvent a crystal is obtained which is then recrystallized from ethanol. In this manner, sesamin, episesamin, sesaminol and episesaminol are obtained from purified sesame oil.

Alternatively, an extract useful for the present invention can be obtained from sesame seeds. In this case, sesame seeds, if necessary after grinding, are extracted with any solvent able to extract the sesame oil, for example, an organic solvent described above. After separating the solvent from the residue, the solvent is evaporated to obtain an extract. An extract obtained from crude sesame oil, or sesame seeds contains lignans such as sesamin, sesaminol, episesamin, episesaminol, sesamolin, 2-(3,4-methylenedioxyphenyl) -6-(3-methoxy-4-hydroxyphenyl)-3,7-dioxabicyclo[3.3.0]-octane, 2,6-bis-(3-methoxy-4-hydroxyphenyl)-3,7-dioxabicyclo[3.3.0-1]octane and 2-(3,4-methylenedioxyphenyl)-6-(3-methoxy-4-hydroxyphenoxy)-3,7-dioxabicyclo[3.3.-0]octane. These lignans can be isolated as described above.

Note, the above-mentioned processes for the isolation of lignans are examples only, and lignans can be obtained by other processes.

Moreover, the present enzyme inhibitors can be used in the form of glycoside derivatives or the like, provided the enzyme inhibitory activity is maintained.

The $\Delta^5$-desaturase inhibitor of the present invention can be used to increase the in vivo level of dihomo-$\gamma$-linolenic acid, and to enhance the dihomo-$\gamma$-linolenic acid cascade, resulting in an increase of the levels of prostaglandin 1 series compounds. On the basis of these properties, the present enzyme inhibitors are promising as medicaments for anti-inflammation, antithrombus, blood pressure lowering activities and the like.

According to the present invention, lignan compounds, piperonyl butoxide, and curcumin can be used alone as the in the present enzyme inhibitory composition, or in an appropriate combination. These compounds are dissolved in ethanol, and the resulting solution is diluted with water before use. Alternatively, the compounds may be formulated as an emulsion in an aqueous solution, or in capsules. Moreover, the present active ingredient can be converted to inclusion bodies with cyclodextrin, which are then formulated to powders, particles, tablets, and other conventional formulations.

The present enzyme inhibitors can also be used in combination with other materials, such as sugars, lipids, proteins or the like, to enhance the effects of the enzyme inhibitors as functional factors. Further, to enhance the effects of the enzyme inhibitors, they may be used in combination with a lipid, for example, a fatty acid having 2 to 20 carbon atoms, such as acetic acid, propionic acid, butyric acid, caproic acid, caprylic acid, capric acid, lauric acid, myristic acid, myristoleic acid, stearic acid, oleic acid, linoleic acid, linolenic acid, arachidic acid, eicosenoic acid, eicosadienoic acid, dihomo-$\gamma$-linolenic acid or the like, alone or in the form of salt such as sodium salt, potassium salt or ammonium salt, ester such as methyl ester or ethyl ester. Moreover, oils containing such fatty acids, for example, conventional oils such as camellia oil, castor oil, chlorophyll oil, corn oil, cottonseed oil, croton oil, linseed oil, olive oil, peanut oil, rapeseed oil, sesame oil, soybean oil, tung oil, whale oil, and coconut oil can be used.

EXAMPLES

The present invention will now be further illustrated by, but is no means limited to, the following examples.

EXAMPLE 1

As a homogenization solution, a 50 mM phosphate buffer (pH 7.4) containing 0.15M KCl, 5 mM $MgCl_2.6H_2O$, 1 mM EDTA, 0.25M saccharose and 1.5 mM glutathione was used. The liver of a Wister male rat was perfused with physiological saline and removed, and to the removed liver was added 4-fold by weight of the homogenization solution, and the whole was homogenized. The homogenate was centrifuged at $10,000 \times g$ for 20 minutes to obtain a supernatant, which was centrifuged at $100,000 \times g$ for one hour to obtain a pellet. The pellet was suspended in the homogenization solution to obtain a microsome solution containing 12.24 mg/ml protein. The above-mentioned procedures were carried out at $4°$ C.

To assay the $\Delta^5$-desaturase activity 100 $\mu$l of the rat liver microsome solution was added to 1 ml of 0.1M phosphate buffer (PH7.4) containing 0.25M saccharose, 0.15M KCl, 1.5 mM glutathione, 45 mM NaF, 0.5 mM nicotinamide, 5 mM $MgCl_2.6H_{20}O$, 7.5 mM ATP, 0.4 mM $CoA.Na_2$, 1.5 mM NADH, and 100 $\mu$M dihomo-$\gamma$-linolenic acid containing 0.1 $\mu$Ci (1.7 nmoles) [2-$^{14}$C]-dihomo-$\gamma$-linolenic acid per 1 ml, the mixture was incubated at $37°$ C for one hour, followed by an addition of 5 ml of ethanol to terminate the reaction. To the reaction mixture was added 1 ml of 4N KOH, and mixture was incubated at $60°$ C for 30 minutes for saponification. After the reaction, 3 ml of water, 100 $\mu$g of dihomo-$\gamma$-linolenic acid and 1 ml of 6N HCl were added thereon, and fatty acids in the reaction mixture were extracted twice with 5 ml of hexane. The extract was evaporated in a centrifuge evaporator and 1 ml of ethyl ether/methanol (9:1) was added to the residue, and the fatty acids were methylated with diazomethane. After allowing to stand at a room temperature for 30 minutes, the reaction mixture was evaporated in a centrifuge evaporator to remove the solvent, whereby methyl esters of the resulting fatty acids were obtained. The esters were separated on a 10% AgNO$_3$ silica gel plate using petroleum ether/ethyl ether (1:1) as a developing solvent. Silica gel portions corresponding to the substrate dihomo-γ-linolenic acid and the product arachidonic acid respectively were peeled off, and to 5 ml of toluene-based scintillation fluid solution was added to the silica gel to measure the radioactivity by a scintillation counter. The radioactivity of the generated arachidonic acid was determined by subtracting a radioactivity at the onset of the reaction from a radioactivity after the reaction.

The enzyme inhibitory activities of sesamin, episesamin and sesamomolin were measured according to the above-mentioned procedure, except that the reaction mixture contained 0.001 to 0.5 mg/ml sesamin, episesamin or sesamolin. The radioactivity was measured as described above, and the percent inhibition was calculated.

For the assay of $\Delta^5$-desaturase and $\Delta^9$-desaturase, substantially the same procedure as described above was repeated, except that 100 nmoles of linoleic acid including 0.1 μCi (1.70 nmoles) of [1-$^{14}$C]-linoleic acid, and 100 nmoles of stearic acid including 0.1 μCi (1.79 nmoles) of [1-$^{14}$C]-stearic acid were used as substrates respectively; and petroleum ether/ethyl ether (7:3) and petroleum ether/ethyl ether (95:5) were used respectively to separate the substrate and product in the thin layer chromatography step. The inhibitory action of sesamin, episesamin and sesamolin on $\Delta^6$-desaturase and $\Delta^9$-desaturase was as described above.

The inhibitory action of sesamin on $\Delta^5$-desaturase, $\Delta^6$-desaturase and $\Delta^9$-desaturase is shown in FIG. 1; and the inhibitory action of episesamin and sesamolin on $\Delta^5$-desaturase and $\Delta^6$-desaturase is shown in FIGS. 2 and 3. As seen from FIGS. 1, 2 and 3, sesamin, episesamin and sesamolin inhibited the $\Delta^5$-desaturation reaction from dihomo-γ-linolenic acid to arachidonic acid.

From this result, it is clear that sesamin, episesamin and sesamolin inhibit $\Delta^5$-desaturase occurring in animals, which inhibit the conversion of dihomo-γ-linolenic acid to arachidonic acid. Moreover, in addition to sesamin, episesamin and sesamolin, it is believed that other lignan compounds can be used, for example, an extract prepared from sesame oil by organic solvent extraction and a component therein such as sesaminol [2-(3,4-methylenedioxy-6-hydroxyphenyl) -6-(3,4-methylenedioxyphenyl)-cis-dioxabicyclo[3,3,0]-octane, episesaminol, as well as an extract from sesame seeds prepared by extraction and a component therein, such as 2-(3,4-methylenedioxyphenyl)-6-(3-methoxy-4-hydroxyphenyl)-3,7-dioxabicyclo[3,3,0]octane, 2,6-bis-(3-methoxy-4-hydroxyphenyl)-3,7dioxabicyclo[3,3,-0]octane and 2-(3,4-methylene -dioxyphenyl)-6-(3-methoxy-4-hydroxyphenoxy)-3,7dioxabicyclo[3,3,0]octane specifically inhibit $\Delta^5$-desaturase in vivo (see Japanese Patent Application No. 63-53642; Japanese Unexamined Patent Publication KOKAI No. H1-243992).

EXAMPLE 2

According to the same procedure as described in Example 1, sesamin, curcumin (Wako Pure Chemical Industries, Japan) or piperonyl butoxide (Aldrich) was added in a reaction mixture at a concentration of 0.03 mg/ml. The result is shown in Table 1.

TABLE 1

| Test compound | Inhibition on $\Delta^5$-desaturase (%) | Inhibition on $\Delta^6$- (%) |
|---|---|---|
| Sesamin | 39.23 | 0 |
| Curcumin | 50.56 | 36.13 |
| Piperonyl butoxide | 32.47 | 0 |

EXAMPLE 3

First, 20 g of sesame oil was dissolved in 150 ml of acetone, and the solution was allowed to stand at −80° C overnight to precipitate an oil fraction. After filtration, the filtrate was evaporated in a rotary evaporator to remove the solvent, and an extract containing lignan compounds such as sesamin, which are $\Delta^5$-desaturase inhibitors, was obtained.

SD male rats 4 weeks old (102 g) were fed for 3 weeks. The feed contained 10% evening primrose oil (EPO) or safflower oil (SFO) as a fat source, and the above-prepared extract in an amount corresponding to 0 g, 10 g or 100 g of sesame oil (test groups were designated EPO-0, EPO-10 and EPO-100, as well as SFO-0, SFO-10 and SFO-100, respectively). After 3 weeks, the body weight, liver weight, plasma cholesterol, plasma triglyceride, plasma lipid, $\Delta^5$-desaturase activity and $\Delta^5$-desaturase activity in liver microsome, PGI$_2$ production by the aorta, and an amount of TXA$_2$ in plasma were measured. The desaturase activity was measured as described in Example 1, and other measurements were carried out according to conventional procedures. The results are shown in Tables 2 and 3.

TABLE 2

| No. | Initial body weight (g) | Final body weight (g) | Increase (g) | Increase/day (g/day) | Tatal feeding taken (g) | Feeding taken/day (g/day) | Efficiency of feeding | Liver weight (g) |
|---|---|---|---|---|---|---|---|---|
| EPO-0 | 102 ± 3 | 270 ± 11 | 167 ± 10 | 8 ± 0 | 384 ± 16 | 18 ± 1 | 0.43 ± 0.01 | 14.57 ± 0.01 |
| EPO-10 | 103 ± 3 | 265 ± 13 | 162 ± 11 | 8 ± 1 | 382 ± 13 | 18 ± 1 | 0.42 ± 0.02 | 14.59 ± 0.83 |
| EPO-100 | 103 ± 2 | 265 ± 10 | 161 ± 8 | 8 ± 0 | 385 ± 13 | 18 ± 1 | 0.42 ± 0.01 | 16.71 ± 0.94 |
| SFO-0 | 103 ± 2 | 269 ± 7 | 166 ± 6 | 8 ± 0 | 385 ± 8 | 18 ± 0 | 0.43 ± 0.01 | 14.49 ± 0.61 |
| SFO-10 | 103 ± 2 | 276 ± 7 | 173 ± 6 | 8 ± 0 | 402 ± 14 | 19 ± 1 | 0.43 ± 0.01 | 14.60 ± 0.78 |
| SFO-100 | 103 ± 2 | 269 ± 7 | 166 ± 5 | 8 ± 0 | 388 ± 9 | 18 ± 1 | 0.43 ± 0.01 | 16.83 ± 0.72 |

| No. | Plasma CHOL (mg/dl) | Plasma TG (mg/dl) | Plasma PL (mg/dl) |
|---|---|---|---|
| EPO-0 | 109.4 ± 5.7 | 189.7 ± 15.8 | 251.8 ± 16.7 |
| EPO-10 | 101.9 ± 6.8 | 165.2 ± 11.6 | 239.0 ± 17.5 |
| EPO-100 | 75.1 ± 4.4 | 149.9 ± 24.9 | 216.3 ± 8.2 |
| SFO-0 | 89.4 ± 2.6 | 253.9 ± 29.2 | 267.7 ± 9.4 |
| SFO-10 | 83.4 ± 4.5 | 175.0 ± 18.9 | 238.3 ± 10.6 |

TABLE 2-continued

| | | | |
|---|---|---|---|
| SFO-100 | 74.8 ± 4.7 | 163.6 ± 14.1 | 222.3 ± 11.7 |

CHOL: cholesterol
TG: triglyceride
PL: phospholipid

TABLE 3

$\Delta^5$- and $\Delta^6$-desaturase activity in rat liver microsome

| (pmol/min/ | EPO | | | SFO | | |
|---|---|---|---|---|---|---|
| mg protein) | 0 | 10 | 100 | 0 | 10 | 100 |
| $\Delta^6$-desaturase activity | 42.1 | 35.0 | 59.4 ↑ | 34.1 | 34.2 | 61.7 ↑ |
| $\Delta^5$-desaturase activity | 48.6 | 39.5 | 34.8 ↓ | 55.5 | 48.8 | 25.2 ↓ |

As seen from the above, the feeding of sesame oil extract for 3 weeks has no influence on the increase of body weight and liver weight, and therefore, does not influence the growth. Moreover, the $\Delta^5$-desaturase activity in microsome was reduced in rats which received the extract. Also, the feeding of the extract provided a tendency toward a lowering of cholesterol levels.

As described above, the present composition comprising $\Delta^5$-desaturase inhibitor can be used specifically to inhibit $\Delta^5$-desaturase occurring in animals, such that an in vivo level of dihomo-γ-linolenic acid increases and prostaglandin 1 series compound is derived from dihomo-γ-linolenic acid and a cascade thereof, resulting in an improvement of inflammation, thrombosis and hypertension conditions. Moreover, the present desaturase inhibitors did not effect $PGI_2$ production by the aorta and an amount of $TXA_2$ in plasma, showing that the present inhibitors do not influence the arachidonic acid cascade.

We claim:

1. A method for inhibiting $\Delta^5$-desaturase in an animal which is in need of $\Delta^5$-desaturase inhibition, which method comprises administering to said animal in need of $\Delta^5$-desaturase inhibition at least a $\Delta^5$-desaturase inhibitory amount of at least one compound selected from the group consisting of sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]-octane,2-(3,4-methylenedioxyphenyl)-6-(3-methoxy-4-hydroxyphenoxy)-3,7-dioxabicyclo[3.3.0]octane, and piperonyl butoxide.

2. A method for inhibiting $\Delta^5$-desaturase in an animal which is in need of $\Delta^5$-desaturase inhibition which method comprises administering to said animal in need of $\Delta^5$-desaturase inhibition at least a $\Delta^5$-desaturase inhibitory amount of an extract of sesame seeds or sesame oil wherein the extract has been prepared using an organic solvent selected from the group consisting of acetone, methyl ethyl ketone, diethyl ketone, methanol and ethanol.

3. A method for inhibiting $\Delta^5$-desaturase in an animal suffering from hypertension or thrombus, which method comprises administering to said animal at least a $\Delta^5$-desaturase inhibitory amount of curcumin.

4. The method of claim 1, wherein the inhibition of $\Delta^5$-desaturase results in treatment of inflammation, thrombosis or hypertension.

* * * * *